US00PP08910P

United States Patent [19]

Davidson

[11] Patent Number: Plant 8,910

[45] Date of Patent: Sep. 27, 1994

[54] HYBRID TEA ROSE PLANT NAMED HADSATIN

[76] Inventor: Harvey D. Davidson, #3 El Verano Rd., Orinda, Calif. 94563

[21] Appl. No.: 137,553

[22] Filed: Oct. 18, 1993

[51] Int. Cl.[5] ..... A01H 5/00

[52] U.S. Cl. ..... Plt./18

[58] Field of Search ..... Plt. 11, 18, 19

*Primary Examiner*—Howard J. Locker

[57] ABSTRACT

A new rose variety of the Hybrid Tea class characterized by having large well formed peach/pink flowers on a thornless bush with glossy foliage.

1 Drawing Sheet

The present invention relates to a new and distinctive variety of rose plant of the Hybrid Tea class, which was originated by my crossing 'Smooth Lady' U.S. Plant Pat. No. 6,147 as the seed parent with 'Smooth Sailing' as the pollen parent.

Among the novel characteristics possessed by the new variety which distinguish it from:

(a) All other varieties of which I am aware are:
- (1) Stems without thorns.
- (2) A very floriferous plant.
- (3) Peach/pink flowers with 35–40 petals.
- (4) Very disease resistant and vigorous.

(b) Seed parent: Pink flowers, 22–24 petals which quill.

(c) Pollen parent: Cream flowers.

Asexual reproduction of the new rose variety by budding, as performed at Tulare, Calif., shows that the aforementioned and all other distinctive characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in the color description herein refers to plate numbers in the aforementioned colour chart, e.g., "53A" is plate "53A" of The Royal Horticultural Society Colour Chart.

Parentage:

*Seed parent.*—'Smooth Lady', U.S. Plant Pat. No. 6,147.

*Pollen parent.*—'Smooth Sailing'.

Class: Hybrid Tea.

The following observations are made of specimens grown outdoors in Contra Costa County, Calif., in the month of September.

FLOWER

Blooming habit:

A. Bud:
- (1) *Size.*—Fully mature, sepals enclosed, 26–28 mm from base of sepals.

- (2) *Form.*—Ovoid.
- (3) *Sepals.*—30 to 36 mm in length; 8 to 10 mm extension beyond bud; no serration shown on sepal edges. Generally 3 out of 5 sepals show appendages on each side, 2 to 5 mm length; heavy cotton matting on inner surface of sepals. Smooth on outer surface. Glandular development on sepal edges. Outside color — 144A; inside — 195A.
- (4) *Peduncle.*—Length — 6 to 7 cm; Surface — smooth, no prickles, a few glandular hairs. Strength — stiff. Color — 144B, with shades of 172B.
- (5) *Receptacle.*—Shape — oblong, 9–10 mm. Color — 144B.
- (6) *Color.*—When sepals first divide, outside petals — 55A shading to 55B, immediate opening inside petals close to 55D.

B. Bloom:
- (1) *Size.*—When open — 11 to 12 cm.
- (2) *Borne.*—Primarily 1 to stem; occassionally 2 to 3.
- (3) *Form.*—Globular.
- (4) *Petalage.*—Average number — 35 to 40.
- (5) *Color.*—Early open 55D inside; 55C outside. Fully open close to 56B inside; 56A outside.

C. Petals:
- (1) *Texture.*—Firm.
- (2) *Appearance.*—Flexed; satiny.
- (3) *Form.*—Rounded; base to top edge: 5 cm; horizontal center: 4.5 cm.
- (4) *Arrangement.*—Regular, well formed.
- (5) *Petaloids in center.*—Average 8 to 10.
- (6) *Persistence.*—Drop off cleanly.
- (7) *Fragrance.*—Strong.
- (8) *Lasting quality.*—On plant 7–8 days; cut 5–6 days.

REPRODUCTIVE ORGANS

A. Stamen:
- (1) *Arrangement.*—Regularly arranged around styles.
- (2) *Number.*—Average 70 to 80.
- (3) *Length.*—Average — 8 to 10 mm.
- (4) *Filaments.*—Color — Close to 47C.
- (5) *Anthers.*—Color — 22A.
- (6) *Pollen.*—22B.

B. Pistil:

(1) *Styles.*—Length — 6 mm exposed; number 80 to 85; many fine white hairs at base; color: near 47B.

(2) *Stigma.*—Color — close to 155A.

(3) *Ovary.*—Shape — oblong; 8–9 mm through center.

C. Hips: Does not set seed.

PLANT

A. Form: Upright.

B. Growth: Vigorous; Height: average 1.4 m.

C. Stem length: Basal break to flower bud tip: average — 70 cm.

D. Foliage: Compound of 3 to 5 leaflets on bloom stem; 5 to 7 leaflets on main canes.

(1) *Mature size.*—5 leaflet — tip of terminal leaflet to stipule base 14–15 mm.

(2) *Quantity.*—Stems well covered.

(3) *Color.*—New foliage upper side 146CB with shades of 184B; under side 184B. Old foliage upper side 147B; under side 146B.

(4) *Shape.*—Oval with center pointed.

(5) *Texture.*—Firm, very leathery, glossy.

(6) *Edge.*—Slight serration on outer edge. Average 8 points per 1 cm, with up to 1 mm peak.

(7) *Rachis.*—Glandular hair on upper side; lower side; 3 to 4 hooked prickles ½–1 mm length, spaced near to 1 cm apart.

(8) *Stipules.*—Length 13–15 mm; auricle to 5 mm. Edge of stipule to tip of auricle with many glandular hairs.

E. Resistance to disease: Mildew, rust, blackspot: excellent.

F. Wood:

*New wood.*—Color 144B. Bark — smooth.

*Old Wood.*—Color 146C. Bark — smooth.

G. Thorns: None.

H. Winter hardiness: Very good.

I claim:

1. A new and distinct variety of rose plant of the hybrid tea class, substantially as herein shown and described.

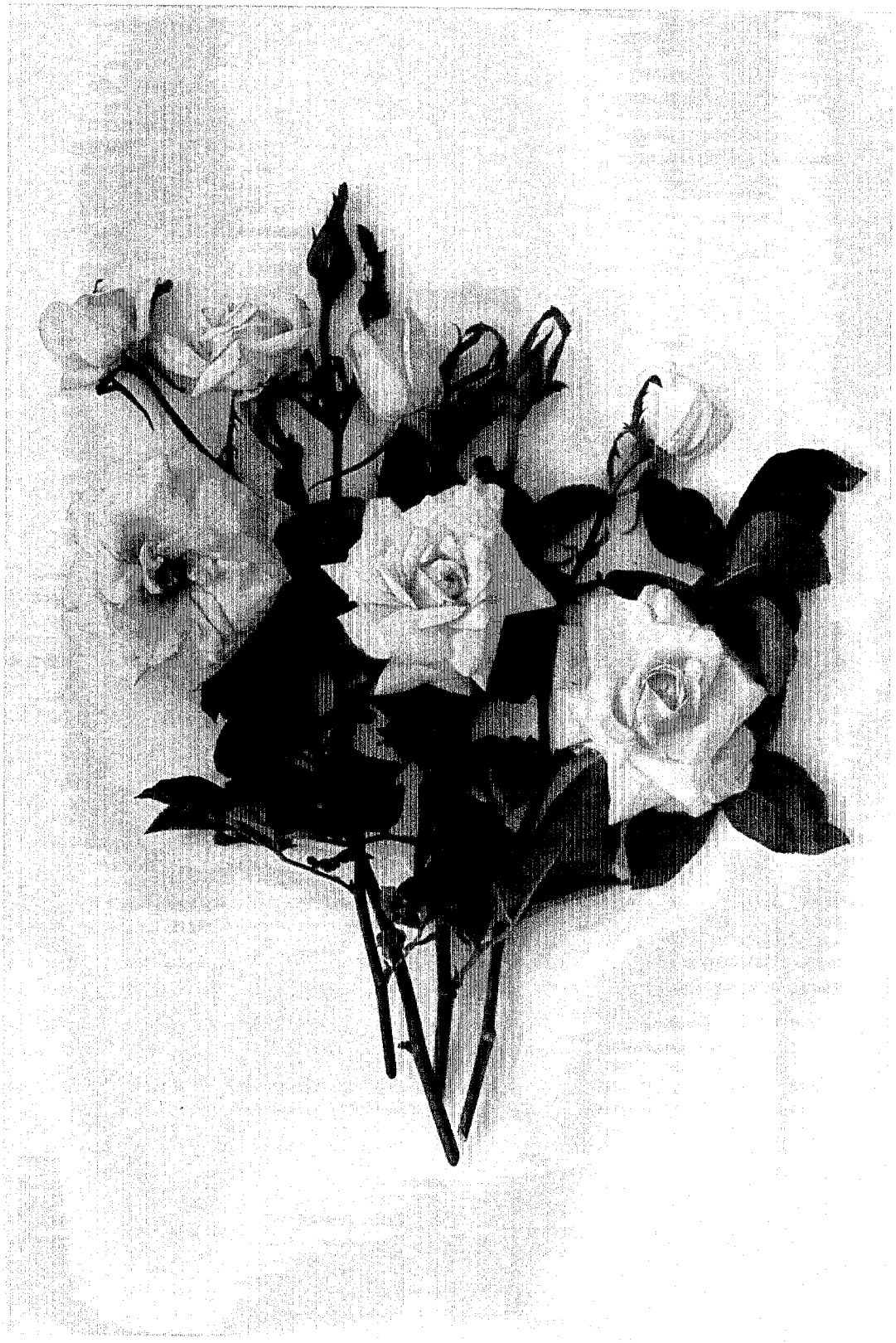

* * * * *